US 6,652,486 B2

(12) United States Patent
Bialecki et al.

(10) Patent No.: US 6,652,486 B2
(45) Date of Patent: Nov. 25, 2003

(54) SAFETY CATHETER

(75) Inventors: Dennis M. Bialecki, Oxford, CT (US); John F. Wuschner, Farmington, CT (US); Mark R. Hillstrand, Southington, CT (US)

(73) Assignee: Medex, Inc., Dublin, OH (US)

( * ) Notice: Subject to any disclaimer, the term of this patent is extended or adjusted under 35 U.S.C. 154(b) by 14 days.

(21) Appl. No.: 09/965,427

(22) Filed: Sep. 27, 2001

(65) Prior Publication Data

US 2003/0060771 A1 Mar. 27, 2003

(51) Int. Cl.⁷ ................................................. A61M 5/00
(52) U.S. Cl. ................................ 604/110; 604/164.08
(58) Field of Search .................... 604/181, 110, 604/161–163, 164.04, 164.08, 164.01, 170.01, 170.02, 171, 174, 180, 192, 197, 198, 263, 117, 158, 264, 168.01, 272–274, 533, 523; 128/919

(56) References Cited

U.S. PATENT DOCUMENTS

| | | |
|---|---|---|
| 4,790,828 A | 12/1988 | Dombrowski et al. |
| 4,828,547 A | 5/1989 | Sahi et al. |
| 4,929,241 A | 5/1990 | Kulli |
| 4,952,207 A | 8/1990 | Lemieux |
| 4,964,854 A | 10/1990 | Luther |
| 4,978,344 A | 12/1990 | Dombrowski et al. |
| 4,994,041 A | 2/1991 | Dombrowski et al. |
| 5,000,740 A | 3/1991 | Ducharme et al. |
| 5,009,642 A | 4/1991 | Sahi |
| 5,049,136 A * | 9/1991 | Johnson ....................... 604/198 |
| 5,053,017 A | 10/1991 | Chamuel |
| 5,085,648 A | 2/1992 | Purdy et al. |
| 5,135,504 A | 8/1992 | McLees |
| 5,183,468 A | 2/1993 | McLees |
| 5,215,525 A | 6/1993 | Sturman |
| 5,215,528 A | 6/1993 | Purdy et al. |
| RE34,416 E | 10/1993 | Lemieux |
| 5,273,540 A | 12/1993 | Luther et al. |
| 5,300,045 A | 4/1994 | Plassche, Jr. |
| 5,334,158 A | 8/1994 | McLees |
| 5,419,766 A | 5/1995 | Chang et al. |
| 5,458,658 A | 10/1995 | Sircom |
| 5,558,651 A | 9/1996 | Crawford et al. |
| 5,611,781 A * | 3/1997 | Sircom et al. ......... 604/164.08 |
| 5,697,907 A | 12/1997 | Gaba |
| 5,882,337 A * | 3/1999 | Bogert et al. ................ 604/110 |
| 6,004,294 A | 12/1999 | Brimhall et al. |
| 6,117,108 A | 9/2000 | Woehr et al. |
| 6,203,527 B1 | 3/2001 | Zadini et al. |
| 6,210,373 B1 | 4/2001 | Allmon |
| 6,224,569 B1 | 5/2001 | Brimhall |
| 6,280,419 B1 * | 8/2001 | Vojtasek ...................... 604/192 |
| 6,287,278 B1 * | 9/2001 | Woehr et al. ............... 604/110 |
| 6,322,537 B1 * | 11/2001 | Chang ................... 604/164.08 |
| 6,379,333 B1 * | 4/2002 | Brimhall et al. ........ 604/164.11 |
| 6,485,468 B2 * | 11/2002 | Vojtasek ...................... 604/192 |
| 6,585,704 B2 * | 7/2003 | Luther et al. ................ 604/263 |
| 6,595,955 B2 * | 7/2003 | Ferguson et al. ........... 604/110 |

FOREIGN PATENT DOCUMENTS

| | | |
|---|---|---|
| WO | 99/08742 A1 | 2/1999 |
| WO | 00/69501 A1 | 11/2000 |

* cited by examiner

*Primary Examiner*—Brian L. Casler
*Assistant Examiner*—Cris L. Rodriguez
(74) *Attorney, Agent, or Firm*—Wood, Herron & Evans, LLP

(57) ABSTRACT

A catheter and introducer needle assembly having a needle attached to a needle hub, and a enlarged area disposed thereon, and a tubular catheter wherein the introducer needle being coaxially received within the catheter. The device has a hollow catheter hub attached to the catheter and in fluid communication therewith. The catheter hub has an interior having a raised annular rib disposed thereon. The assembly includes a needle tip protector disposed within the catheter hub and including at least one unrestrained radially extending lip disposed distal to the annular rib so as to retain the protector within the hub. The distal end of the protector does not abut against the hub interior. The protector has a proximal opening at the proximal end having an unrestrained size greater than the size of the needle diameter and smaller than the enlarged area such that when the needle is removed from the catheter the protector remains attached to the needle.

12 Claims, 8 Drawing Sheets

SAFETY CATHETER

FIELD OF THE INVENTION

The present invention relates, in general, to intravenous (IV) catheters and, more particularly, to a safety IV catheter with a needle tip protector that will automatically cover the needle tip upon needle withdrawal.

BACKGROUND OF THE INVENTION

I.V. catheters are used primarily to administer fluids directly into a patient's vascular system. The catheter is inserted into a patient's vein by a clinician using a handheld placement device that includes a needle with a sharp distal end. The needle is positioned in the interior hollow portion of the catheter with its sharp distal tip extended slightly beyond the distal edge of the catheter. The proximal end of the needle is connected to a needle hub which is held by the clinician during the insertion procedure.

During the insertion procedure, the clinician inserts the needle and catheter together into the patient's vein. After insertion of the needle point into the vein, the catheter is forwarded into the vein of the patient by the clinician pushing the catheter with their finger. The clinician then withdraws just the needle by grasping the hub attached to the proximal end of the needle while at the same time applying pressure to the patient's skin at the insertion site, thus holding the catheter fixed in place. The clinician then typically tapes the proximal end of the now inserted catheter to the patient's skin and connects the proximal end of the catheter, containing a Luer connector catheter hub, to the source of the fluid to be administered into the patient's vein.

It is the period of time just as the needle is withdrawn from the catheter that poses great risk to the clinician. The clinician is at risk of an accidental needle stick from the sharp needle which has just been contaminated with a patients blood. This leaves the clinician vulnerable to the transmission of dangerous blood-borne pathogens, including hepatitis and AIDS. The risk of a contaminated needle stick is not isolated just to clinicians. Careless disposal of used needles can put other health care workers at risk as well. Even others outside the health care profession, for example those involved in the clean-up and final disposal of medical waste, are at risk of an accidental needle stick from a carelessly discarded needle.

A number of "safety" IV catheters have been developed to address the issue of accidental needle stick. For example, in U.S. Pat. No. Re. 34,416 to Lemieux, a safety catheter is disclosed which includes an element which covers the needle tip upon removal of the needle from the catheter. The safety element includes a split flange at its proximal end which is expanded by the needle as the needle is inserted into an undersized hole at the center of this flange. The safety element is thus held secure within the catheter hub by inserting the needle through the undersized hole which forces the outside perimeter of the split flange against the inside wall of the catheter hub.

One of the drawbacks to this design is the amount of friction force exerted against the needle by the split flange. A tight fit of the flange against the catheter wall causes great friction against the needle making it difficult to be withdrawn from the catheter by the clinician. A loose fit leaves the flange prone to releasing prematurely from the catheter as the needle is withdrawn, creating the potential that the needle tip will be left exposed.

In U.S. Pat. No. 6,117,108 to Woehr et al, a safety IV catheter is described including a resilient needle guard which protects the needle tip upon removal of the needle from the catheter hub. The needle guard includes an arm that includes an opening through which a needle passes causing radial movement of the arm. This radial movement forces the arm into a groove or behind a rib located on the inside of the catheter hub, capturing the needle guard in the catheter hub. A potential issue with this design develops when the needle guard is not properly seated into the catheter hub. If the distal end of the needle guard arm is not in alignment with the groove in the catheter hub, excessive forces are placed on the needle causing a high drag force as the clinician removes the needle. And, since the needle guard arm is not properly seated in the groove, it may prematurely release from the catheter hub upon the removal of the needle leaving the needle tip exposed.

The prior art safety catheters all exhibit one or more drawbacks that have thus far limited their usefulness and full acceptance by health-care workers. What is needed therefore is a safety IV catheter that functions reliably, is easy and inexpensive to manufacture, and easy to use.

SUMMARY OF THE INVENTION

In accordance with the present invention there is provided a catheter and introducer needle assembly including a needle having a diameter, proximal end, attached to a needle hub, a distal end, and a enlarged area disposed therebetween. The assembly further includes a tubular catheter having proximal and distal ends, the introducer needle being coaxially received within the catheter, and a hollow catheter hub having a distal end attached to the proximal end of the catheter and in fluid communication with the catheter. The catheter hub includes an interior having a raised annular rib disposed thereon. The assembly also includes a needle tip protector having a proximal end and a distal end disposed within the catheter hub. The proximal end including at least one unrestrained radially extending lip disposed distal to the annular rib so as to retain the protector within the hub, wherein the distal end of the protector does not abut against the hub interior. The protector having a proximal opening at the proximal end having an unrestrained size greater than the size of the needle diameter and smaller than the enlarged area such that when the needle is removed from the catheter the protector remains attached to the needle.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

As used herein, the term "proximal" refers to a location on the catheter and needle assembly with needle tip protector closest to the clinician using the device and thus furthest from the patient on which the device is used. Conversely, the term "distal" refers to a location farthest from the clinician and closest to the patient.

Figure 1:
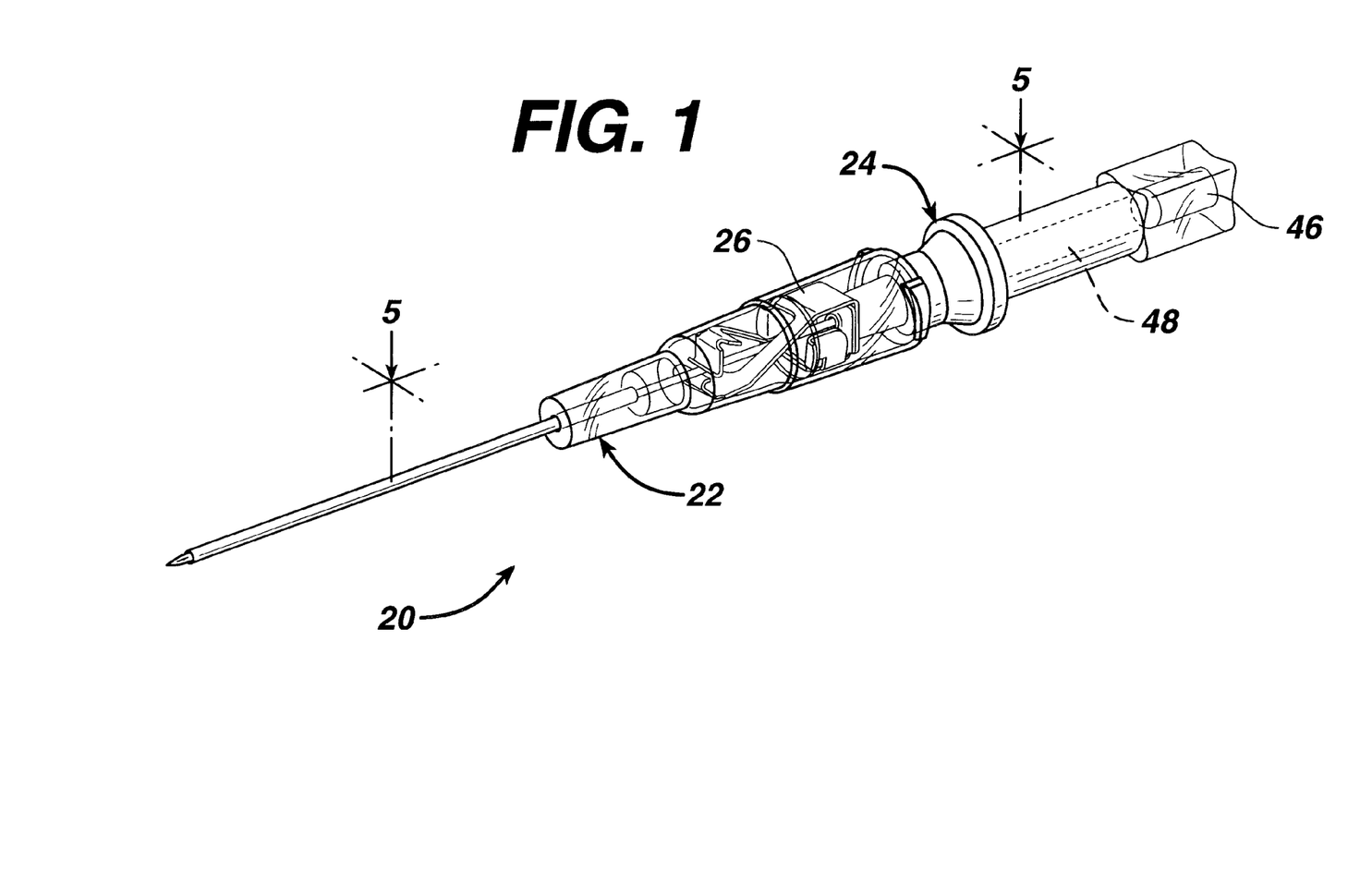
FIG. 1 is a perspective view of the catheter and needle assembly of the present invention.
Figure 2:
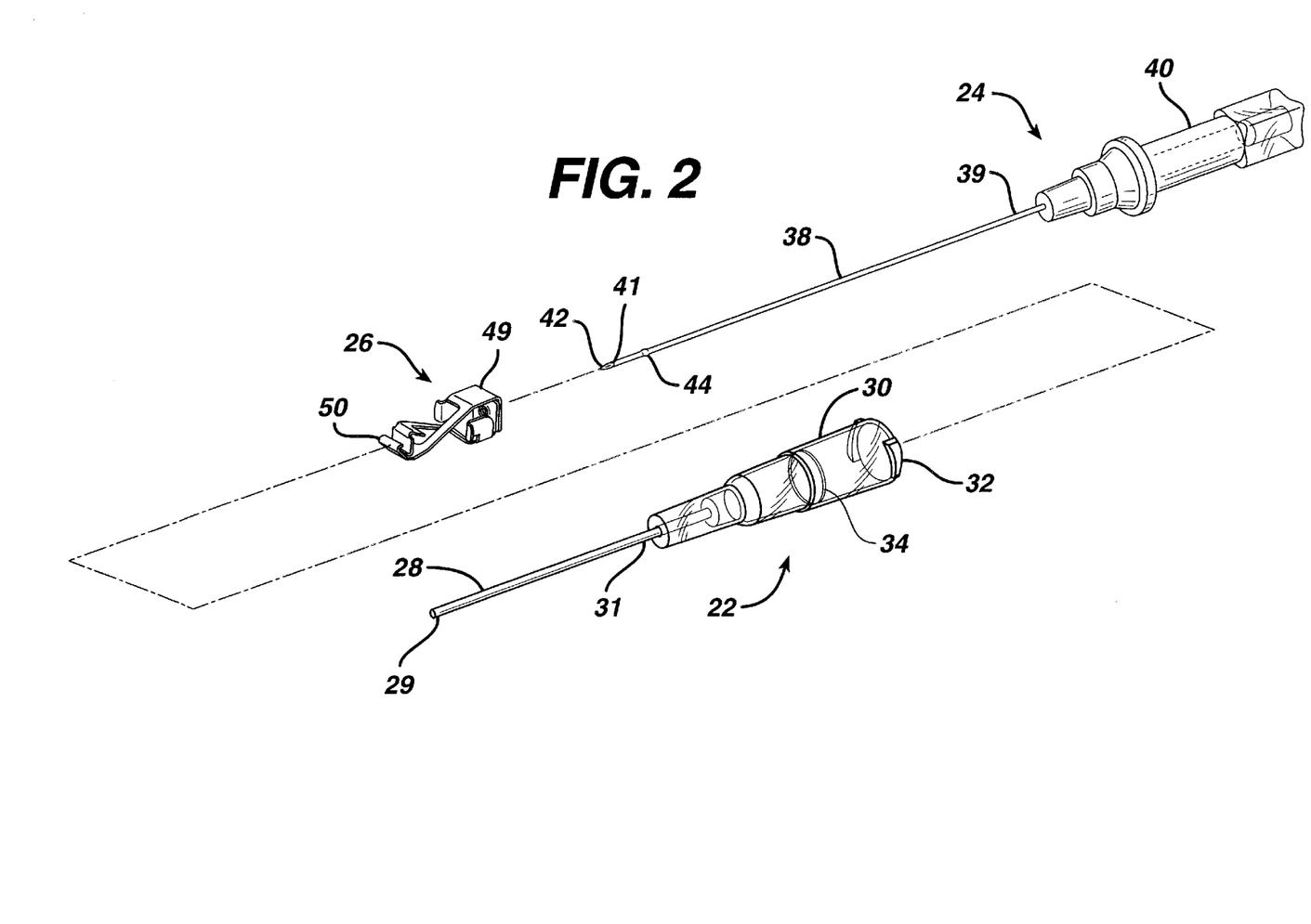
FIG. 2 is an exploded perspective view of the catheter assembly and needle assembly including the needle tip protector of the present invention.
Figure 5:
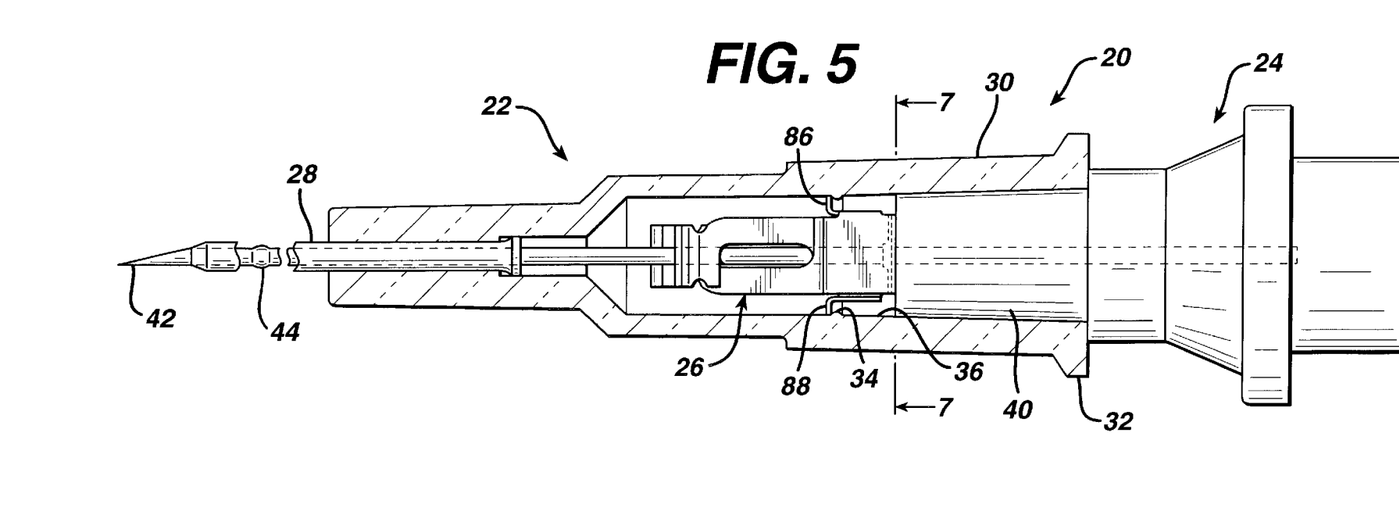
FIG. 5 is a section view of the catheter assembly and needle assembly taken along line 5—5 of FIG. 1.
Figure 6:
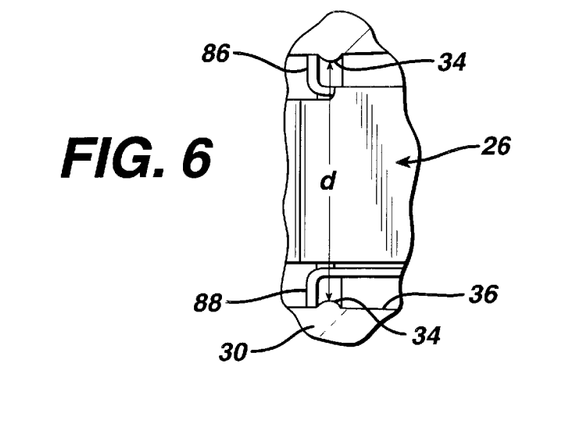
FIG. 6 is an enlarged partial section view of FIG. 5 illustrating the relative position of the needle tip protector tab and catheter hub rib.

As illustrated in FIGS. 1 and 2, IV catheter assembly 20 comprises catheter assembly 22 and needle assembly 24. Needle assembly 24 further includes needle tip protector 26. Catheter assembly 22 includes catheter 28 which is a tubular structure having a proximal end 31 and distal end 29. Proximal end 31 of catheter 28 is fixedly attached to catheter hub 30. Catheters are well known in the medical art and one of many suitable materials, most of which are flexible thermoplastics, may be selected for use in catheter 28. Such materials may include, for example, polyurethane or fluorinated ethylene propylene. Catheter hub 30 is a generally tubular structure having an internal cavity in fluid communication with the internal lumen of catheter 28. Catheter hub 30 may be made from a suitable, rigid medical grade thermoplastic such as, for example, polypropylene or polycarbonate. For illustration purposes catheter hub 30 is shown translucent, though in actual use it may be translucent or opaque. At the proximal end of catheter hub 30 is integrally attached Luer fitting 32, commonly known in the medical art. Luer fitting 32 provides for secure, leakproof attachment of tubing, syringes, or any of many other medical devices used to infuse or withdraw fluids through the catheter assembly. As is more clearly illustrated in FIGS. 5 and 6, rib 34 is a raised annular ring integral to and extending from internal sidewall 36 of catheter hub 30. Rib 34 is located approximately mid way between the proximal end and distal end of sidewall 36. Rib 34 plays an important role in securing needle tip protector 26 in catheter hub 30, as will be described in more detail later.

Referring again to FIGS. 1 and 2, needle assembly 24 comprises needle 38, which is a tubular structure with a proximal end 39 and distal end 41, needle hub 40, and needle tip protector 26. Needle tip protector 26 is assembled slidably on needle 38. Needle 38 is preferably made of stainless steel. Proximal end 39 of needle 38 is fixedly attached to needle hub 40. A bevel 42 is located at the most distal end of needle 38 creating a sharp piercing tip. Needle crimp 44 is located at the distal end of needle 38 proximal to bevel 42 and is larger in diameter than the nominal diameter of needle 38. Needle crimp 44 is created by "coining" an area on the outside diameter of needle 38 resulting in two opposed bumps located approximately 180 degrees across the center axis of needle 38. Coining is a process well known in the metal forming art and involves using a hardened tool to strike a softer object to deform or displace a portion of the softer object. In the present case a portion of the exterior surface of the softer metal needle 38 is displaced by a harder metal tool so as to raise bumps on the exterior surface of needle 38. The resulting crimp 44 is larger in dimension than the nominal diameter of needle 38. Crimp 44 is larger in dimension than the diameter of second flange hole 72 in needle tip protector 26 and is important in preventing the complete removal of needle tip protector 26 from needle 38, as will be described in more detail later. In the preferred embodiment the dimension across crimp 44 is 0.0001–0.004 inches larger than second flange hole 72, dependant upon needle "gauge" size.

Needle hub 40 is generally a tubular structure having an internal cavity in fluid communication with the lumen in needle 38. It is preferably made of a translucent or transparent generally rigid thermoplastic material such as, for example, polycarbonate. At the most proximal end of the internal cavity in needle hub 40 is fixedly attached porous plug 46. A flashback chamber 48 is created in the cavity distal to porous plug 46. Porous plug 46 contains a plurality of microscopic openings which are large enough to permit the passage of air and other gasses but small enough to prevent the passage of blood. Flashback chamber 48 fills with blood upon successful entry of the needle tip into the targeted vein, providing the clinician visual conformation of the correct placement of the needle.

Referring now to all figures, needle tip protector 26 has a proximal end 49 and distal end 50 and is preferably a unitary structure formed from a single piece of thin, resilient material, preferably stainless steel. First flange 66 and second flange 68 are generally square and are integrally connected at right angles to first outer wall 74 and second outer wall 76, respectively. First outer wall 74 is connected at a right angle to first tab flange 78. First tab flange 78 and second tab flange 80 are each formed at angles slightly greater than 90 degrees to second outer wall 76 so that the resulting dimension c is slightly larger than inside diameter d (see FIGS. 6–7) across rib 34 in catheter hub 30. In the preferred embodiment angles a and b are each approximately 94.25 degrees. In the preferred embodiment dimension c is approximately 0.001–0.009 inches larger than dimension d. First flange hole 70 is located in the center of first flange 66 and is over-sized to slidably receive needle 38. Second flange hole 72 and skirt 82 are located in the center of second flange 68. Skirt 82 is integral to second flange hole 72 and is formed by extruding material from second flange hole 72 in a direction distal to second flange 68. This permits for a very close but slidable fit over the nominal diameter of needle 38. Skirt 82 also functions to help maintain alignment of needle 38 to the center axis of needle tip protector 26. As would be understood by one skilled in the art, flange hole 72 would be appropriately sized to the particular needle "gauge" size to which it is designed to receive.

First tab 86 and second tab 88 are connected at right angles to first tab flange 78 and second tab flange 80, respectively, and protrude outward away from the center axis of needle tip protector 26. First tab edge 90, located on the outer portion of first tab 86, and second tab edge 92, located on the outer portion of second tab 88, are each arcuate to approximately match the curve of sidewall 36 in catheter hub 30.

Figures 3, 4:
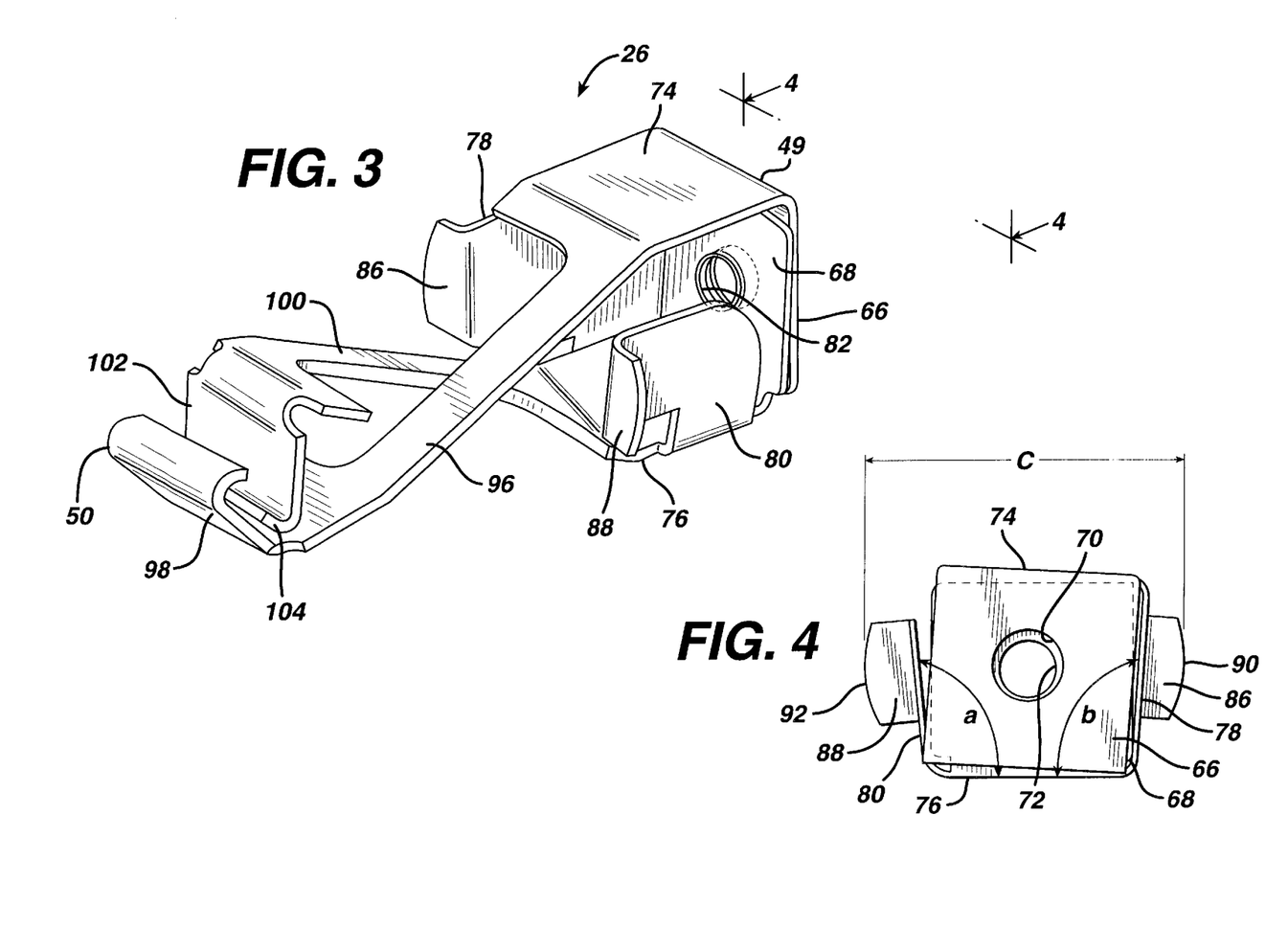
FIG. 3 is a perspective view of the needle tip protector of the present invention.
FIG. 4 is an elevation view of FIG. 3 taken along line 4—4 illustrating the hole positions in the rear flanges of the needle tip protector as manufactured.

Referring again to FIG. 3, first beam 96 extends distally from first outer wall 74 and is angled toward and extends past the center axis of needle tip protector 26. At the distal end of first beam 96 is integrally formed curved first lip 98 which extends across and through the center axis of needle tip protector 26. Second beam 100 extends distally from second outer wall 76 and is angled toward and extends past the center axis of needle tip protector 26. At the distal end of second beam 100 is stop flange 102 which extends across and normal to the center axis of needle tip protector 26. At the end of stop flange 102 opposite its connection to second beam 100 is integrally formed curved second lip 104.

Figure 8:
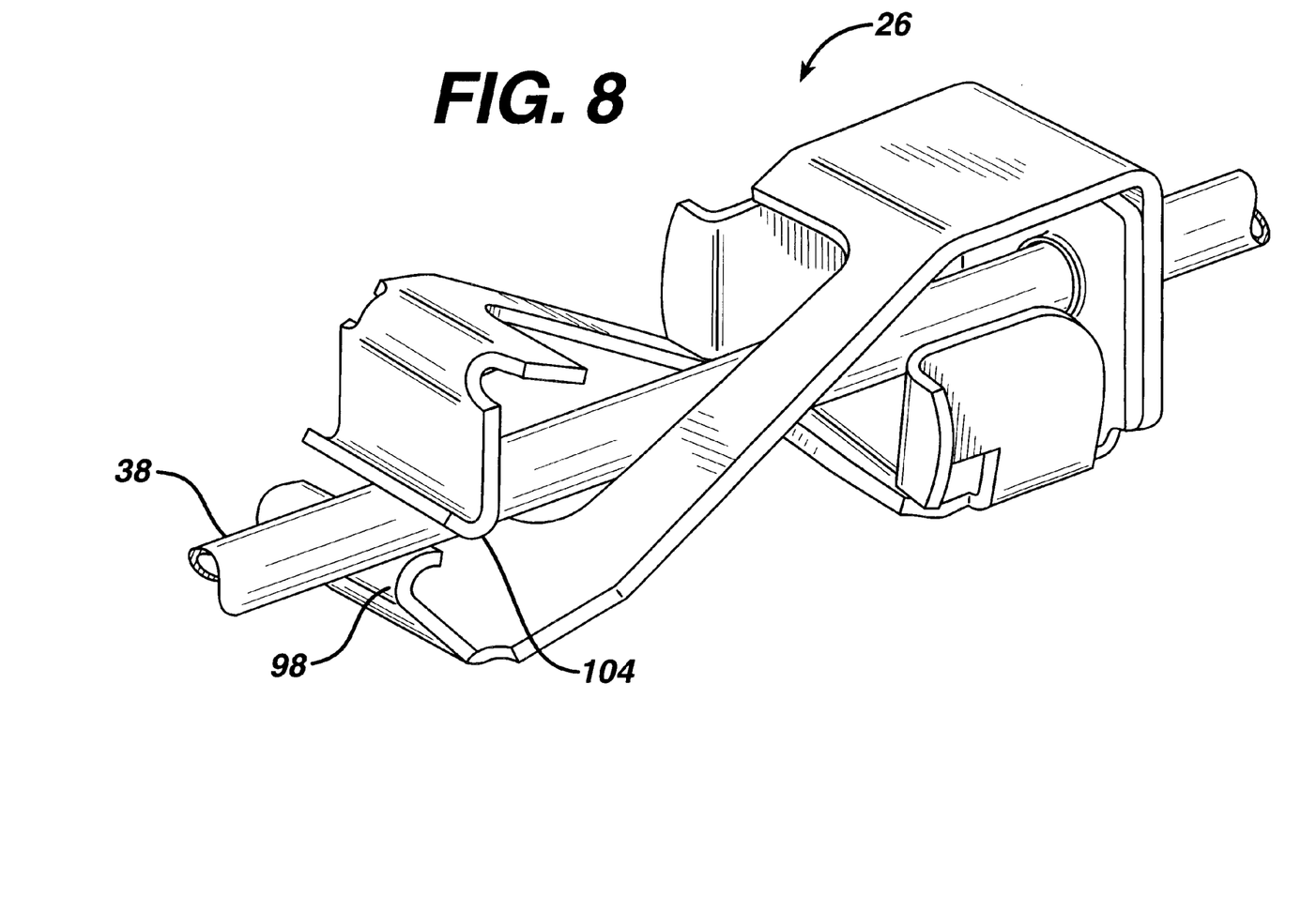
FIG. 8 is a perspective view of the needle tip protector shown as installed in the catheter hub with the needle inserted there through, catheter hub not shown for clarity.
Figure 9:
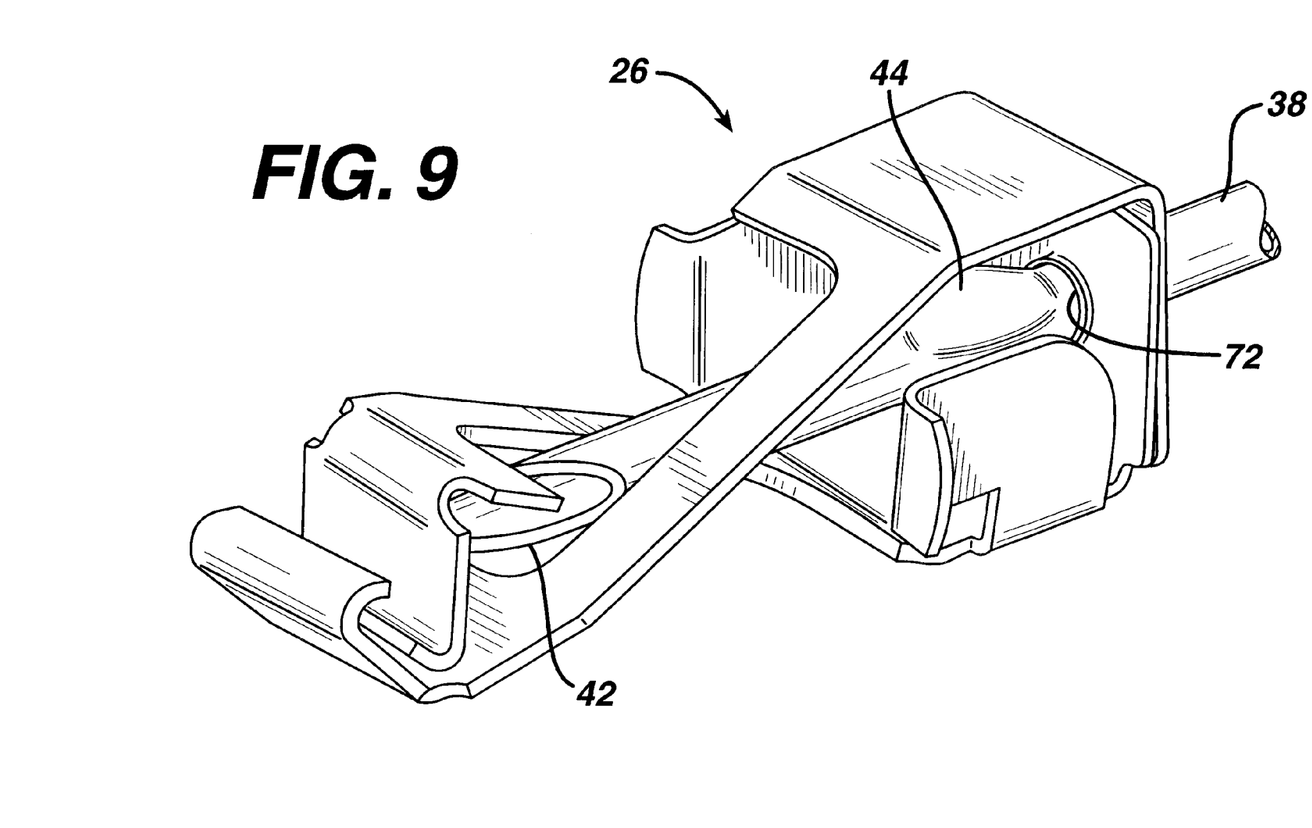
FIG. 9 is a perspective view of the needle tip protector shown as removed from the catheter hub and illustrating the needle tip covered by the protector.

Referring now to all figures, needle tip protector 26 is assembled to needle 38 as follows;

- The proximal end of needle 38 is fixedly attached to the distal end of needle hub 40, which contains porous plug 46 fixedly attached to its proximal end;
- The distal end of needle 38 is inserted through first flange hole 70 and then through second flange hole 72 in needle tip protector 26, moving from proximal to distal;
- First beam 96 and second beam 100 are flexed, as a result of their resilient properties, normal to the center axis of needle tip protector 26 so that needle 38 will pass between first lip 98 and second lip 104 (see FIG. 8);
- Needle crimp 44 is added to the distal end of needle 38 just proximal to bevel 42. Crimp 44 increases the diameter of needle 38 locally to a dimension larger than the inside diameter of second flange hole 72 (see FIG. 9) thus preventing the complete removal of needle tip protector 26 from the distal end of needle 38.

Now needle assembly 24, including needle tip protector 26, is assembled into catheter assembly 22 as follows;

- The distal end of needle 38 is positioned into the proximal end of catheter hub 30 and needle assembly 24 is moved distally causing needle 38 to enter catheter 28;
- As needle assembly 24 continues to move distally, needle tip protector 26 enters the opening in the proximal end of catheter hub 30,
- Continued distal movement of needle assembly 24 causes the distal edge of needle hub 40 to push first tab 86 and second tab 88 on needle tip protector 26 into contact with rib 34 located on hub sidewall 36;
- Continued distal movement forces first tab 86 and second tab 88, due to the resilient properties of needle tip protector 26, past rib 34 and in contact with sidewall 36, just distal to rib 34.

Needle tip protector 26 is thus held distal to rib 34 inside the cavity in catheter hub 30 by the flexural forces of first tab 86 and second tab 88 since dimension c on needle tip protector 26 is larger than dimension d across rib 34 inside catheter hub 30. (see FIG. 6).

Figure 7:
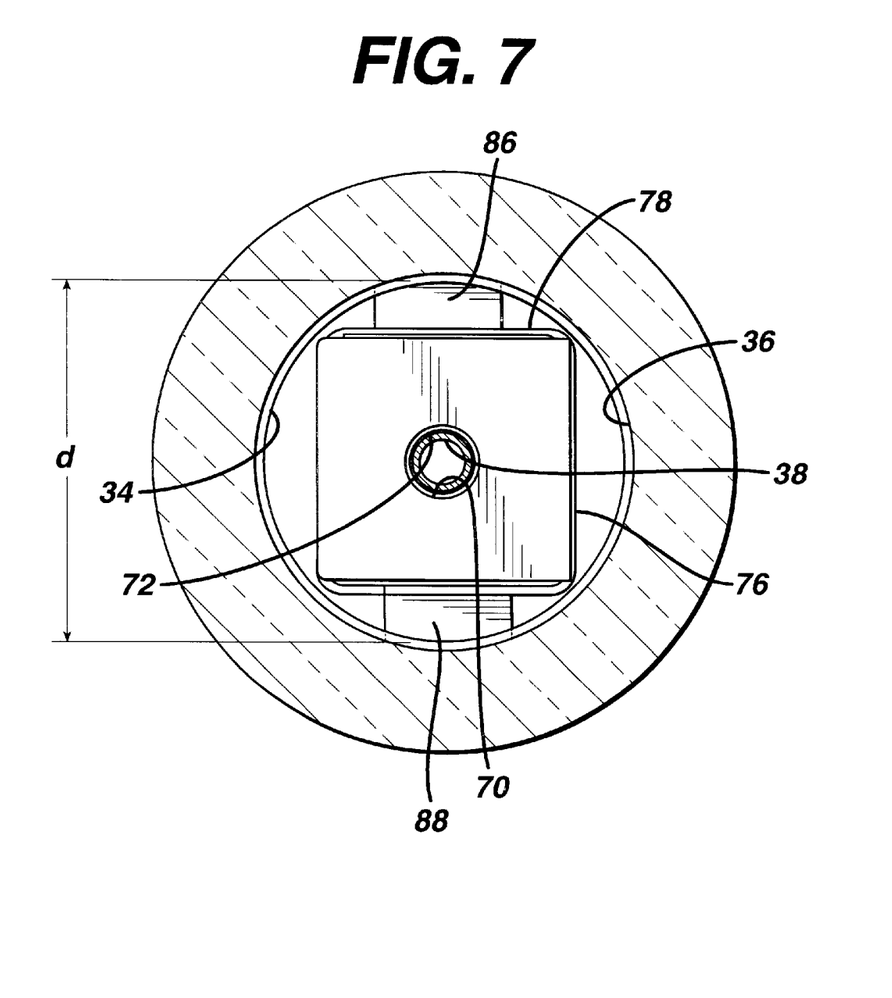
FIG. 7 is a section view of the catheter hub with needle tip protector installed taken along line 7—7 of FIG. 5.

As is best illustrated in FIG. 7, the movement of first tab 86 and second tab 88 as needle tip protector 26 is finally seated distal to rib 34 causes flexure in second outer wall 76 and first tab flange 78 resulting in the approximate alignment of first flange hole 70 and second flange hole 72.

Figure 10:
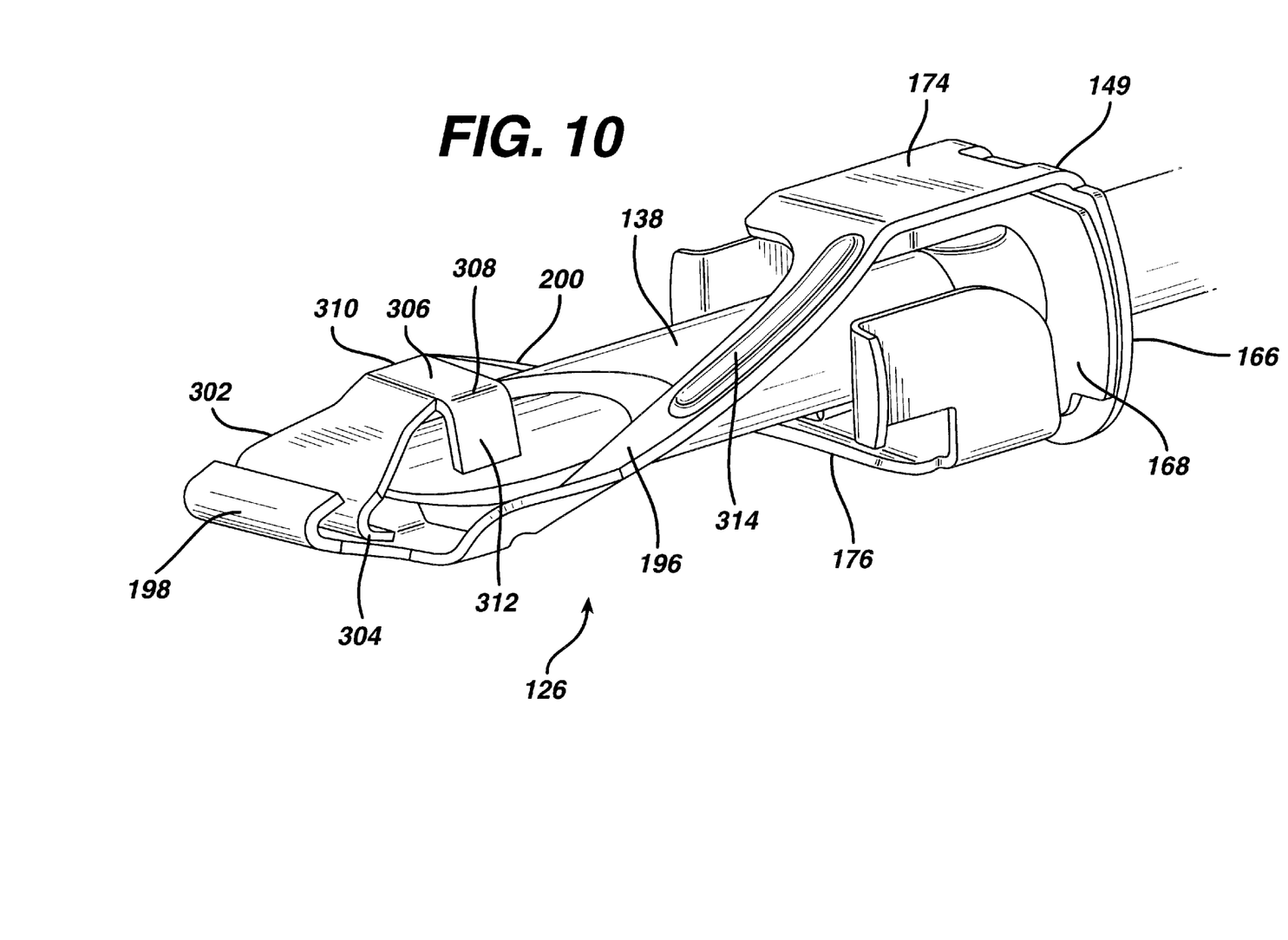
FIG. 10 is a perspective view of an alternate embodiment of the needle tip protector of the present invention.

Now, in actual clinical use, the IV catheter assembly 20 of the present invention functions as follows;

- The distal end of needle 38 which extends just past the distal end of catheter 28 is inserted into the patient's vein;
- The clinician observes blood in the flash chamber in needle hub 40;
- The clinician grasps needle hub 40, and catheter assembly 22 alone is moved distally into the vein;
- The clinician applies slight pressure to the insertion site to hold catheter assembly 22 secure;
- The clinician grasps the needle hub and begins withdrawal of needle assembly 24 from catheter assembly 22. During this process, needle tip protector 26 remains secure inside catheter hub 30 until raised crimp 44 on the distal end of needle 38 comes into contact with second flange hole 72. Just before raised crimp 44 encounters second flange hole 72, the biasing forces of first beam 96 and second beam 100 cause stop flange 102 and first lip 98 to move normal to and across the center axis of needle 38, blocking any further distal movement of needle 38 relative to needle tip protector 26;
- Since crimp 44 is larger than second flange hole 72, continued proximal movement of needle 38 carries needle tip protector 26 proximal as well, forcing first tab 86 and second tab 88 on needle tip protector 26 against rib 34. First tab 86 and second tab 88 are forced to flex normal to and toward the center axis of needle tip protector 26, permitting continued movement proximal, past rib 34;
- Needle assembly 24 is now removed entirely from catheter assembly 22, with the needle tip covered by needle tip protector 26 of the present invention.
- FIG. 10 shows an alternate embodiment of the present invention. In this embodiment, needle tip protector 126, is preferably a unitary structure formed from a single piece of thin, resilient material such as, for example, stainless steel, similar to needle tip protector 26. Needle tip protector 126 includes first flange 166 and second flange 168. First flange 166 and second flange 168 are generally arcuate and are integrally connected to first outer wall 174 and second outer wall 176, respectively. Extending distally from first outer wall 174 of needle tip protector 126 is first beam 196. First beam 196, which has an arcuate outer edge, is angled toward and extends past the center axis of needle tip protector 126. First beam 196 further includes first rib 314 coined therein to add stiffness.

At the distal end of first beam 196 is integrally formed curved first lip 198 which extends across and through the center axis of needle tip protector 126. Extending distally from second outer wall 176 of needle tip protector 126 is second beam 200. Second beam 200, which has an arcuate outer edge, is angled toward and extends past the center axis of needle tip protector 126. Second beam 200 further includes second rib 316 (not visible) coined therein to add stiffness. The distal end of second beam 200 is connected to the proximal end of wing base 306. Wing base 306 extends across and parallel to the center axis of needle tip protector 126. Wing base 306 further comprises first wing side 308 and second wing side 310. Integrally attached to first wing side 308 of wing base 306 at approximately a 90° angle is wing 312. Wing 312, which extends parallel to the center axis of needle tip protector 126, prevents any further radial movement of needle 138 by retaining it within needle tip protector 126. Connected to the distal end of wing base 306 is the proximal end of stop flange 302. Stop flange 302 extends across needle 138 and is angled toward the center axis of needle tip protector 126. At the distal end of stop flange 302 opposite its connection to wing base 306 is integrally formed curved second lip 304. Second lip 304 is curved toward proximal end 149 of needle tip protector 126 to prevent any further distal movement of needle 138.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims. In addition, it should be understood that every structure described above has a function and such structure can be referred to as a means for performing that function.

What is claimed is:

1. A catheter and introducer needle assembly, comprising:
   a) a needle having a diameter, a proximal end attached to a needle hub, a distal end, and an enlarged area disposed therebetween;
   b) a tubular catheter having proximal and distal ends, said introducer needle being coaxially received within said catheter;
   c) a hollow catheter hub having a distal end attached to said proximal end of said catheter and in fluid communication with said catheter, said catheter hub including an interior having a raised annular rib disposed thereon; and
   d) a needle tip protector having a proximal end and a distal end disposed within said catheter hub, said proximal end including at least one unrestrained radially extending lip disposed distal to said annular rib so as to retain said protector within said hub, said distal end of said protector does not abut against said hub interior, said protector having a proximal opening at said proximal end having an unrestrained size greater than said size of said needle diameter and smaller than said enlarged area such that when said needle is removed from said catheter said protector remains attached to said needle.

2. The catheter and introducer needle assembly of claim 1 wherein said enlarged area on said needle is 0.0001–0.004 inches larger than said needle diameter.

3. The catheter and introducer needle assembly of claim 1 wherein said annular rib has an inner diameter that is 0.001–0.009 inches smaller than the distance across said lip on said needle tip protector.

4. The catheter and introducer needle assembly of claim 1 wherein said distal end of said needle tip protector is biased to abut against said needle.

5. The catheter and introducer needle assembly of claim 1 wherein said lip further comprises an outer edge that is generally arcuate.

6. A catheter and introducer needle assembly, comprising:
   a) a needle having a diameter, a proximal end attached to a needle hub, a distal end, and an enlarged area disposed therebetween;
   b) a tubular catheter having proximal and distal ends, said introducer needle being coaxially received within said catheter;
   c) a hollow catheter hub having a distal end attached to said proximal end of said catheter and in fluid communication with said catheter, said catheter hub including an interior having a raised annular rib disposed thereon; and
   d) a needle tip protector having a proximal end and a distal end disposed within said catheter hub, said proximal end including at least one unrestrained radially extending lip disposed distal to said annular rib so as to retain said protector within said hub, said distal end of said protector does not abut against said hub interior, said protector having a proximal opening at said proximal end having an unrestrained size greater than said size of said needle diameter and smaller than said enlarged area such that when said needle is removed from said catheter said protector remains attached to said needle, said protector further comprising an outer wall, a first tab flange, a second tab flange, said first tab flange attached to said outer wall at an angle greater than 90 degrees, and said second tab flange attached to said outer wall, opposite said first tab flange, at an angle greater than 90 degrees.

7. The catheter and introducer needle assembly of claim 6 wherein said enlarged area on said needle is 0.0001–0.004 inches larger than said needle diameter.

8. The catheter and introducer needle assembly of claim 6 wherein said annular rib has an inner diameter that is 0.001–0.009 inches smaller than the distance across said lip on said needle tip protector.

9. The catheter and introducer needle assembly of claim 6 wherein said distal end of said needle tip protector is biased to abut against said needle.

10. The catheter and introducer needle assembly of claim 6 wherein said lip further comprises an outer edge that is generally arcuate.

11. The catheter and introducer needle assembly of claim 6 wherein said angle between said outer wall and said first tab flange is 94.25 degrees.

12. The catheter and introducer needle assembly of claim 6 wherein said angle between said outer wall and said second tab flange is 94.25 degrees.

* * * * *